United States Patent
Reminiac et al.

(10) Patent No.: US 7,829,343 B2
(45) Date of Patent: Nov. 9, 2010

(54) METHOD AND DEVICE FOR DETERMINING THE SMOKE POINT OF HYDROCARBONS

(75) Inventors: Myriam Reminiac, Mougeot le Havre (FR); Pierre Pestiaux, Senneville sur Fécamp (FR)

(73) Assignee: Total Raffinage Marketing, Puteaux (FR)

( * ) Notice: Subject to any disclaimer, the term of this patent is extended or adjusted under 35 U.S.C. 154(b) by 568 days.

(21) Appl. No.: 11/722,770

(22) PCT Filed: Dec. 28, 2005

(86) PCT No.: PCT/FR2005/003294

§ 371 (c)(1),
(2), (4) Date: Jun. 25, 2007

(87) PCT Pub. No.: WO2006/072708

PCT Pub. Date: Jul. 13, 2006

(65) Prior Publication Data

US 2008/0020479 A1    Jan. 24, 2008

(30) Foreign Application Priority Data

Dec. 30, 2004  (FR) .................................. 04 14087

(51) Int. Cl.
*G01N 31/12* (2006.01)
*G01N 31/00* (2006.01)
(52) U.S. Cl. .................. 436/143; 436/139; 422/78; 422/68.1; 422/50
(58) Field of Classification Search .................. 436/143, 436/139; 422/78, 68.1, 50; 356/36
See application file for complete search history.

(56) References Cited

U.S. PATENT DOCUMENTS

| | | | |
|---|---|---|---|
| 2,819,607 A | | 1/1958 | Hunt, Jr. et al. |
| 3,811,839 A | * | 5/1974 | Di Pietro et al. .............. 422/59 |
| 4,865,444 A | * | 9/1989 | Green et al. .................. 356/36 |
| 4,988,846 A | * | 1/1991 | Karlsten et al. ........ 219/137.61 |
| 5,627,643 A | * | 5/1997 | Birnbaum et al. ........... 356/344 |
| 2002/0144455 A1 | | 10/2002 | Bertrand et al. |
| 2003/0128737 A1 | * | 7/2003 | McGrath et al. ............ 374/161 |

OTHER PUBLICATIONS

Patent Abstracts of Japan, vol. 013, No. 361 (P-917), Aug. 11, 1989 & JP 01 119764 A (Showa Yotsukaichi Sekiyu KK), May 11, 1989 Abstract.

* cited by examiner

*Primary Examiner*—Walter D Griffin
*Assistant Examiner*—Christine T Mui
(74) *Attorney, Agent, or Firm*—Sughrue Mion, PLLC

(57) ABSTRACT

The invention relates to a method for determining the smoke point of a hydrocarbon, comprising, among the different steps defined in the ASTM D 1322 standard or equivalents thereof, the identification, among different aspects of the flame according to the position of the burner in the lamp, of a particular aspect of the flame and the reading of the height of this flame on a graduated scale in mm. The invention is characterized by the fact that a series of digital images of the flame is taken and recorded with the aid of a digital camera or the like at intervals sufficiently close for permitting, by analyzing these digital images, the detection of a sudden change in the shape of the flame, and that the height of this flame is measured at the moment of this sudden change in its shape, said height being considered as the smoke point of the tested hydrocarbon.

23 Claims, 2 Drawing Sheets

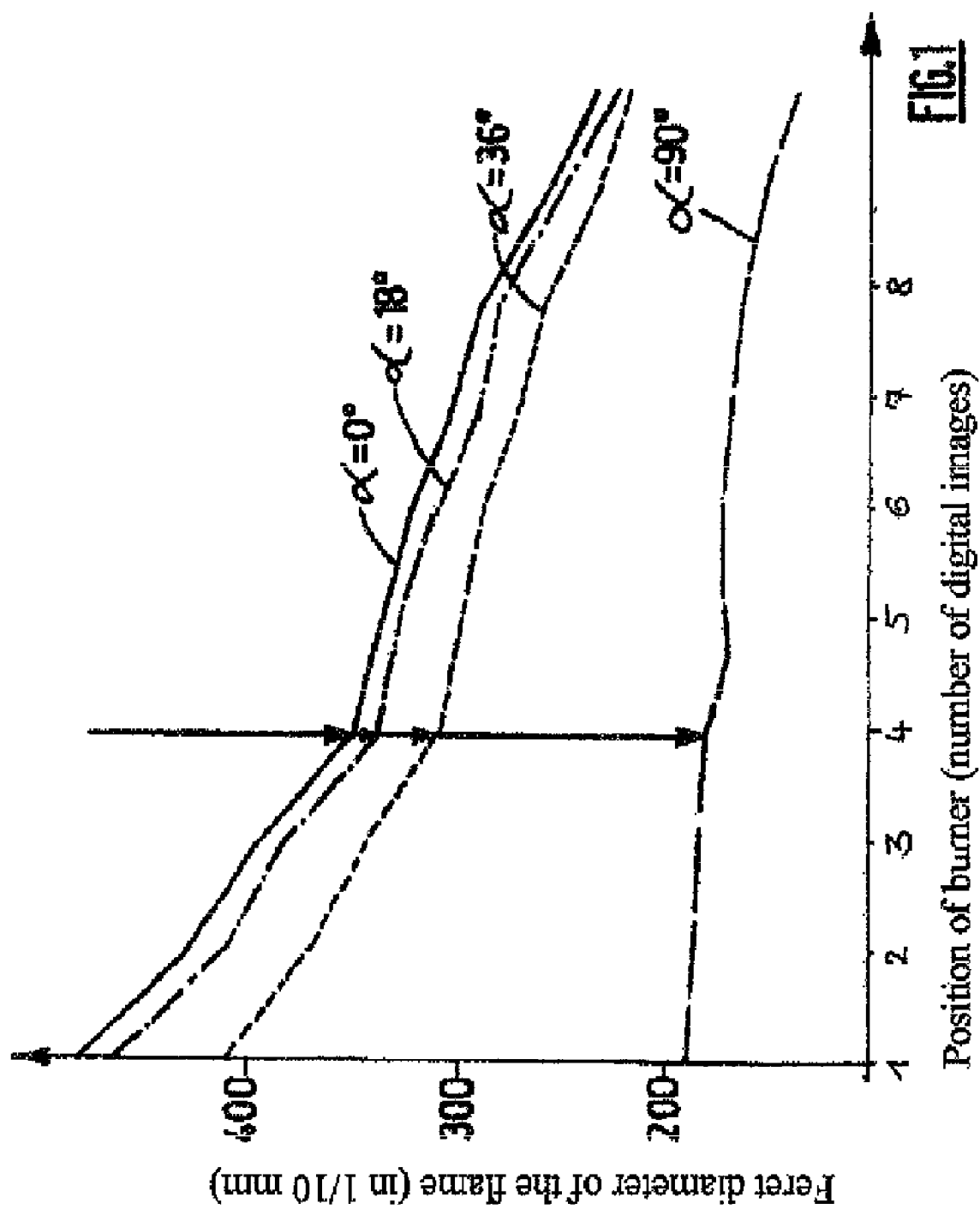

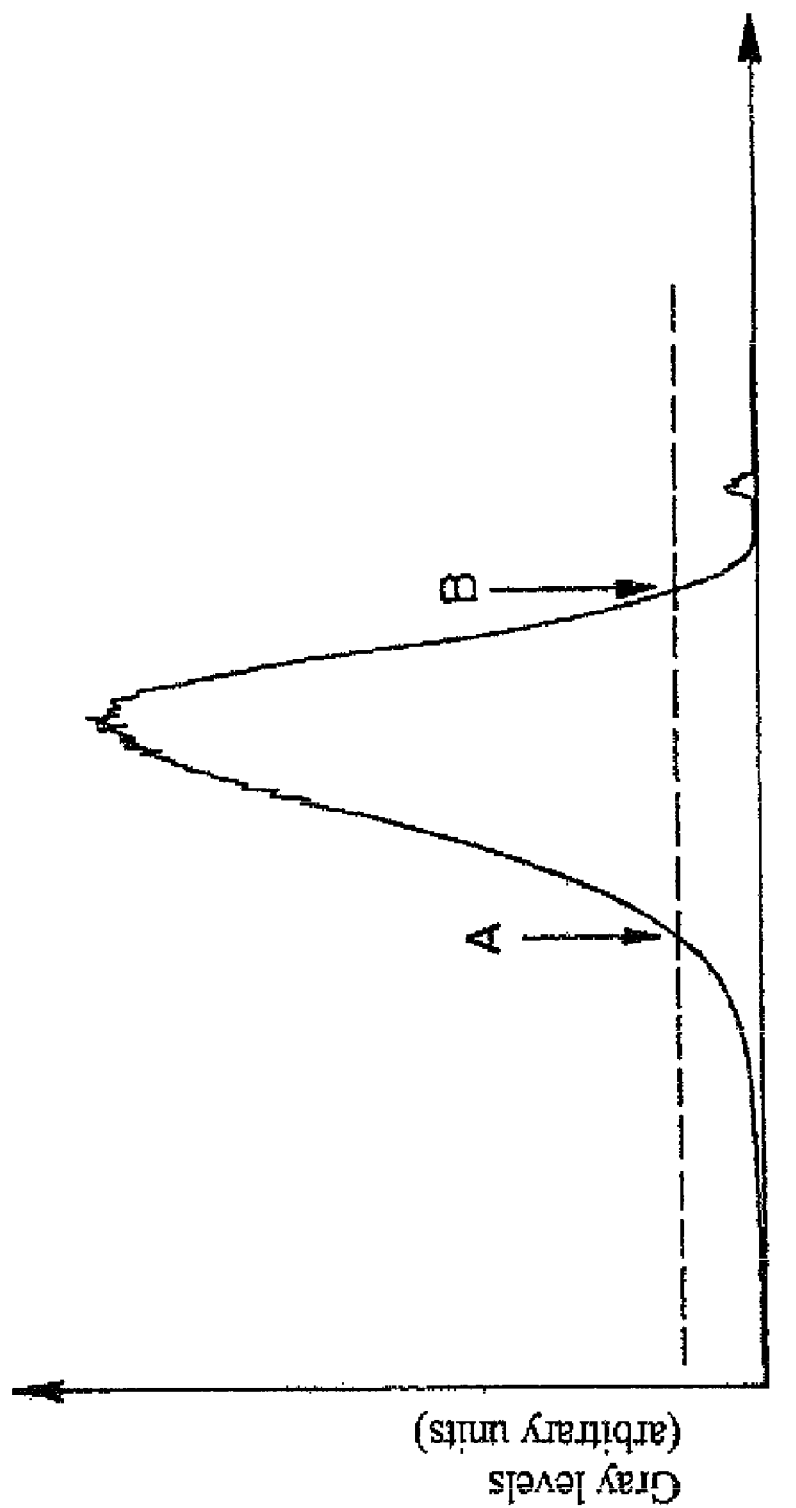

METHOD AND DEVICE FOR DETERMINING THE SMOKE POINT OF HYDROCARBONS

The present invention relates to an improved method for determining the smoke point of hydrocarbons, comprising in particular the acquisition and analysis of digital images, and a device for implementing such a method.

BACKGROUND OF THE INVENTION

The smoke point of a hydrocarbon is a characteristic that is routinely determined in the laboratories of refineries, mainly on kerosenes, aviation fuels and even lamp oils.

This characteristic is an important parameter since it is directly linked to the hydrocarbon composition of the fuels under test. In practice, the greater the C/H ratio, and therefore the lower the aromatic compound content, the higher the smoke point becomes and the better the fuel behaves on its combustion. In other words, the smoke point is quantitatively linked to the potential transfer of radiative heat and, in as much as this heat transfer exerts a strong influence on the temperature of the metallic parts, the smoke point therefore becomes a predictive indicator of the longevity of said metallic parts.

The smoke point does, unfortunately, however have the drawback of being fairly difficult to measure. Normally, for this, an analysis method is used that is the subject of a standardization (such as the method described in the ASTM D 1322 standard and its equivalents, such as ISO 3014, IP 57 and NF M 07-028) to enable the detection, then the measurement of the maximum height of a flame (normally expressed in mm and accurate to the nearest tenth of an mm) which can be obtained from the hydrocarbon under test without the formation of smoke.

In such a measurement, the sample is burned in a wick lamp, also described in the ASTM D 1322 standard, and the operator varies the position of the burner so as to gradually modify the height and the appearance of the flame, which changes slowly from a relatively elongated and jumpy state with a top end giving off a light smoke, to a state in which the flame height is shorter, with a top end that is perfectly rounded. Between these two flame states, the operator must also distinguish two other intermediate shapes, namely that having an elongated point, the edges of which appear concave in the top part and the one in which the pointed end has just disappeared and which forms a flame that is slightly rounded without smoke. It is when the flame has this last appearance that the operator records the height of the flame, on a scale graduated in mm positioned inside and at the back of the lamp. The final value of the smoke point retained for the sample under analysis is the average of three successive measurements, calculated to the nearest 0.1 mm.

The method of measuring the smoke point, as defined in the ASTM D 1322 standard, like all the analysis methods of this type, does, however, have limitations in terms of accuracy, mainly due to the assessment difficulties of the operator, in particular when taking the decision to judge the correct appearance of the flame, according to the standard, and also at the moment when the height of this flame is measured visually on the graduated scale. In practice, the good quality of the measurement of this height requires particular procedural precautions, the application of which depends entirely on the operator. Thus, the repeatability and reproducibility of the standardized test are respectively 2 mm and 3 mm.

The Applicant has proposed to remedy this difficulty by replacing the eye and the brain of the operator with a technical system or acquiring digital images mainly comprising a digital camera, or an equivalent of such a digital camera, and an associated computer system for analyzing and processing the stored digital images. However, the distinguishing of the different characteristic shapes of the flame, between the relatively elongated and jumpy state with a top end giving off a light smoke and the state presenting a shorter flame height with a top end that is perfectly rounded, is subjective and is ill-suited to the normal use of a computer program for analyzing and processing digital images. The Applicant, after much research work, has found that, surprisingly, the use of such a system associated with a choice of appropriate parameters and a correct calibration, would make it possible to spectacularly increase the accuracy of the method and obtain the smoke point of the hydrocarbon under test but without the problem of the subjectivity of the operator.

SUMMARY OF THE INVENTION

The subject of the invention is, consequently, a method for determining the smoke point of a hydrocarbon, comprising among the different steps defined in the ASTM D 1322 standard or its equivalents, the identification, among different appearances of the flame according to the position of the burner in the lamp, of a particular appearance of the flame and the reading of the height of this flame on a scale graduated in mm, characterized in that a series of digital images of the flame is taken and stored using a digital camera or an equivalent of such a camera, at intervals that are sufficiently close to enable, by analyzing these digital images, the detection of a sudden change in the shape of the flame, and that the height of said flame is measured at the moment of this sudden change in its shape, said height being considered as the smoke point of the hydrocarbon under test.

Preferably, the digital camera will be equipped with a photodetecting charge-coupled device (CCD). The image-taking intervals will preferably be between 0.1 and 2.0 seconds, and in particular between 0.5 and 1.0 second. The number of digital images of each series of images is preferably at least equal to 10.

The digital image-taking operations and the analysis and processing of these images to identify the image corresponding to the first sudden change in the shape of the flame are preferably automated using a dedicated software package.

BRIEF DESCRIPTION OF THE DRAWINGS

FIG. 1 depicts the trend of the Feret diameter according to the lowering of the position of the burner during the step (h) of the method of the present invention; and FIG. 2 represents the value of the gray levels of a line of pixels passing mid-height through the flame, perpendicular to the vertical axis of symmetry of the flame.

DETAILED DESCRIPTION OF THE INVENTION

The various steps of the known method of measuring the smoke point discussed above and referred to in the preamble to the independent method claim, carried out in the procedural conditions defined in the ASTM D 1322 standard, or its equivalents, are as follows:

(a) preparing and calibrating a lamp for determining the smoke point as indicated in the standard, points 9 and 10, (b) fitting a wick measuring at least 125 mm, soaked with sample, in the wick-holder of the lamp's burner, (c) introducing 20 ml of sample into the burner's tank, (d) screwing the wick-holder with the wick onto the burner's tank, (e) cutting the top end of the wick so that it extends above the wick-holder by 6 mm and inserting the burner into the lamp, (f) lighting the wick and adjusting the wick until the flame has a height of approximately 1 cm and, after a combustion period of approximately 5 minutes, (g) raising the burner until smoke appears, then, (h) slowly lowering the burner until the flame no longer gives off smoke and presents a top end that is perfectly rounded, The steps preliminary to identifying the sudden change in the shape of the flame are strictly in accordance with the ASTM D 1322 standard (in particular the ASTM D 1322-97 standard), or one of its technical equivalents, so there is no need to describe in detail here all the procedural conditions and safety measures making it possible to correctly carry out the method of determining the smoke point.

The step consisting in manually gradually lowering the wick of the lamp's burner to obtain a flame no longer giving off smoke and presenting a top end that is slightly rounded, of the method of the present invention, differs, however from the corresponding step (h) of the method of the ASTM D 1322 standard by the fact that a series of digital images of the flame is acquired and stored, and the stored digital images are analyzed using an appropriate image analysis system, so as to be able to deduce from it the maximum height of the flame that does not give off smoke, in other words the smoke point of the fuel under test.

To understand the invention better, the Applicant first describes the visual assessment of the maximum height of the flame that does not give off smoke as provided by the ASTM D 1322 standard, by here providing a partial transcription of point 11.4 of this standard:

11.4 Light the burner and adjust the wick so that the flame has a height of approximately 10 mm and leave the lamp burning for approximately 5 minutes. Raise the burner until smoke appears, then lower the burner slowly passing through the following flame appearance steps:

11.4.1 a long point, smoke weakly visible, flame erratic and jumpy, 11.4.2 an elongated point with lateral edges that are concave towards the top (flame A), 11.4.3 pointed end just disappears, leaving a flame that is very slightly 'blunted' (flame B), 11.4.4 a well rounded point (flame C). Determine the height of the flame B to the nearest 0.5 mm. Make a note of the observed height.

11.4.4.1 To eliminate parallax errors, the eye of the observer must be slightly to one side of the central line so that the reflected image of the flame is visible on the graduated scale to one side of the central vertical white line and the flame itself is visible against the other side of the graduated scale. The results of the two readings should be identical.

In the method of the present invention, the technical system for storing and analyzing images used to replace the eye of the observer serves both to determine the moment when the visible flame corresponds to the "flame B" of the standard, and to measure as accurately as possible the height of this flame B.

Analysis of the digital images stored while the burner is being lowered that is accompanied by the reduction in the size of the flame, has shown that the sudden change in the shape of the flame, that is, the appearance of the "flame B", corresponded to a sudden change, that is easy to detect, in the speed of reduction of the Feret diameter of the image of the flame. The Feret diameter of an object is equal to the distance between two tangents to the object, parallel to each other, and defining an angle α relative to the horizontal, this angle being sometimes called "direction of measurement of the Veret diameters". When the object is not a circle, this distance depends on the angle α defined by the tangents relative to the horizontal.

It will easily be understood that, in the case of the flame whose dimensions are to be measured, the distance between two tangents to the flame, parallel to each other and to the horizontal (α=0°) is equal to the height of the flame. This is why, in the description below, the height of the flame is sometimes called Feret diameter with angle α=0°.

The analysis of the images as such, whether analyzing the shape of the flame or its height, requires an additional operation, called "thresholding" or "binarization", conventionally used in analyzing and processing digital images. This thresholding operation consists in setting to zero all the pixels having a gray level less than a certain value, called "threshold", and to 1 all the pixels having a value above the threshold.

In practice, a flame is a physical phenomenon characterized by a local increase in heat and light intensity. Although the human eye believes it can distinguish a fairly clear and precise flame outline, the digital image in terms of gray levels of a flame shows that the increase in light intensity is continuous and that there is a gradual change to increasingly higher brightnesses. This brightness continuity appears clearly in FIG. 2 which represents the value of the gray levels of a line of pixels passing mid-height through the flame, perpendicular to the vertical axis of symmetry of said flame.

The sudden change in the speed of reduction of the Feret diameter, corresponding to the moment at which the "flame B" appears, is preferably determined by different measurements of the Feret diameter at an angle α that is other than zero. This angle α nevertheless has a relatively low value, preferably less than 45°. FIG. 1 shows, for four different angles α (0°, 18°, 36° and 90°), the trend of the Feret diameter (in ¹⁄₁₀ mm) according to the lowering of the position of the burner during the step (h) of the method. On the three curves respectively corresponding to an angle α=0°, 18° and 36°, a break point is observed, indicated by an arrow, where the slope of the curve (reflecting the speed of reduction of the height of the flame) changes suddenly. This break point or "fold" corresponds to the moment when the flame is a flame B in the sense of the ASTM D 1322 standard, for a precise position of the burner. It will be noted that, for an angle α=90° (Feret diameter corresponding to the width of the flame), this characteristic break point is not observed.

After determining the position of the burner corresponding to the flame of maximum height not giving off smoke (flame B), secondly, the absolute height of this flame is determined which, after the appropriate corrections, gives the smoke point.

The absolute value of the height of the flame B is determined by comparing it with a graduated scale which is part of the lamp described in the ASTM D 1322 standard. In the known method, the operator directly reads the height of the flame B on the graduated scale, placed behind said flame, taking the precautions indicated in point 11.4.4.1. In the inventive method, the graduated scale is not visible on the digital image of the flame stored by the CCD digital camera. The height of the flame must consequently be determined by superimposing the digital image of the flame on the digital image of the graduated scale (calibration image), taken independently by the CCD apparatus from an identical position, but in the absence of flame, and with appropriate lighting.

As for the detection of the shape of the flame corresponding to the flame B, in the sense of the ASTM D 1322 standard, determining the height of the flame also entails a digital image thresholding operation.

In practice, to determine the height of a flame, it is necessary first to decide the light intensity from which the flame begins. This decision amounts to setting a threshold (gray level value) above which it is considered that there is a flame, and below which it is considered that there is no flame. In FIG. 2, the chosen threshold corresponds to the dashed horizontal line. The arrows A and B mark the limits of the flame for this threshold.

The difficulty lies in choosing the threshold to be used. In practice, the higher the chosen threshold is, the lower the absolute value of the height of the flame that will be obtained becomes. The appropriate threshold that is, the threshold that gives the absolute height of the flame leading to the correct smoke point of the fuel under test can be determined using one or more standard fuel mixtures (toluene/2,2,4-trimethylpentane), for which the ASTM D 1322 standard indicates the smoke point. For this, a correctly installed apparatus is used to produce a series of digital images of a combustion flame of a standard fuel mixture, and, after an appropriate thresholding operation as indicated above, the digital image corresponding to the sudden change in the speed of reduction of the Feret diameter is selected, then this image is subjected to a series of thresholding operations with different thresholds and the threshold that gives a flame height equal to the smoke point indicated by the ASTM D 1322 standard for the standard fuel mixture used is retained. The duly determined threshold must be retained throughout the series of measurements.

To complement the automation of the measurement of the smoke point of a hydrocarbon, according to the present invention, an ancillary continuous servo-control device between the position of the burner in the lamp and the triggering of image-taking by the digital camera can be installed, the burner being in this case positioned at different levels in the lamp by means of an electric motor.

Another subject of the present invention is a device for determining the smoke point of a hydrocarbon fuel. comprising:

(A) an apparatus for determining the smoke point conforming to the specifications of the ASTM D 1322 standard,
(B) a digital camera, preferably a CCD digital camera, and, linked to said camera,
(C) a computer system designed and programmed to enable digital images taken by the digital camera to be stored, analyzed and processed.

This device also preferably comprises an anti-infrared filter placed between the apparatus for determining the smoke point (A) and the digital camera (B), and which serves to intercept the infrared radiation emitted by the flame that would saturate the images and render them unusable.

The CCD device digital camera preferably covers wavelengths ranging from the ultraviolet to the infrared, but models covering only the visible spectrum or the visible-UV spectrum can, however, also be used. The use of an anti-infrared filter then becomes superfluous.

The dynamic range of the digital camera used to acquire the digital images is not a determining factor. To obtain images offering a satisfactory resolution, at least 10-bit CCD digital cameras should however be used, making it possible to store digital images with at least 512 gray levels. 16-bit or higher CCD digital cameras giving images with 32 768 gray levels, or more, are particularly preferred.

The CCD digital camera normally comprises a zoom and is placed at a distance of approximately 1 m to 1.5 m from the lamp of the apparatus for determining the smoke point. The zoom is then set so that the stored digital image contains the image of all the graduated scale of the apparatus for determining the smoke point. It is essential for the relative position of the CCD digital camera, relative to the lamp, not to vary between two images. The invariability of this position is, in effect, the essential condition that makes it possible to compare the different stored images and the smoke point values calculated from the latter. If, however, the position of the digital camera or the zoom setting were altered inadvertently, a new calibration image (image of the graduated scale in the absence of flame) can and must be acquired.

Given the very high sensitivity of the sensors of CCD digital cameras, a certain number of measures must be taken to ensure a good image quality. The different protocols for calibrating and eliminating background noise are familiar to those skilled in the art using CCD sensors and do not need to be described in detail here. As an example, measures ensuring a good image quality, cooling of the CCD sensors by a Peltier module, in order to eliminate the formation of so-called "thermal" charges, can be cited.

The present invention is illustrated by the following exemplary applications.

EXAMPLE 1

Validation of the Method According to the Invention by Determination of the Smoke Point of a Fuel Mixture with Known Smoke Point—determination of an Appropriate Threshold After having installed and calibrated the wick lamp and the device according to the present invention, two successive series, each of ten digital images, are taken of a combustion flame of a mixture of 15% by volume of toluene and 85% by volume of 2,2,4-trimethylpentane (reference smoke point: 25.8 mm), the height of which is gradually reduced in accordance with the protocol described in point 11.4 of the ASTM D 1322 standard. Based on the digital images obtained, previously subjected to a thresholding of a value equal to approximately 15% of the measurement range of the CCD sensor, i.e., for this test, a value of 2000, a curve of the value of the Feret diameter of the flame is plotted, for a measurement direction $\alpha$ of this same Feret diameter equal to 36°, according to the position of the burner, or more precisely, according to the image number. A sudden change in the speed of reduction of the height of the flame is observed for the image number 4. Various thresholding operations are then applied to this image and the threshold that gives a Feret diameter at $\alpha=0°$ that is the closest to the theoretical value of the standard (25.8 mm) is retained. The duly determined threshold of 4000 gives a Feret diameter ($\alpha=0°$) of 26.2 mm for the first series of images and 25.9 mm for the second series of images.

The software for analyzing and processing the two series of ten digital images, used in the present test, is supplied by Neosis, marketed by the same Visilog 6. The threshold values retained and the values of the angle $\alpha$ for the calculation of the corresponding Feret diameters were determined previously using different reference products according to the present invention in the procedural conditions conforming to the ASTM D 1322 standard.

EXAMPLE 2

Repeatability of the Flame Height Measurement
With a device according to the invention comprising:
(a) an apparatus for measuring the smoke point according to the ASTM D 1322 standard,
(b) a CCD digital camera (16 bits) provided with a zoom, (c) linked to the digital camera, a computer with the Visilog 6 software published by Neosis installed, capable of storing, analyzing then processing the digital images originating from the digital camera, and (d) an anti-infrared filter placed between (a) and (b) three successive series, each of four digital images, are acquired, respectively corresponding to four different heights of a combustion flame of a hydrocarbon to be analyzed. The duly obtained digital images are subjected to a thresholding operation with a threshold equal to 4000, determined in the example 1.

The following flame height values are obtained (expressed in mm):

| Series No. | Flame 1 | Flame 2 | Flame 3 | Flame 4 |
|---|---|---|---|---|
| 1 | 15.9 | 11.4 | 9.4 | 5.6 |
| 2 | 15.9 | 11.2 | 9.4 | 5.6 |
| 3 | 16.1 | 11.2 | 9.2 | 5.7 |
| Average | 15.9 | 11.3 | 9.3 | 5.6 |
| Standard deviation | 0.1 | 0.1 | 0.1 | 0.1 |
| Calculated repeatability | 0.3 | 0.3 | 0.3 | 0.3 |
| ASTM D 1322 repeatability | 2 | 2 | 2 | 2 |

It can be seen that the standard deviations are of the order of 0.1 mm.

The repeatabilities obtained with the method and the device according to the present invention are of the order of 6 to 7 times better than those stated in the ASTM D 1322 standard.

The invention claimed is:

1. A method for determining the smoke point of a hydrocarbon, comprising:
   among the different steps defined in the ASTM D 1322 standard, identifying, among different appearances of the flame according to the position of the burner in the lamp, of a particular appearance of the flame; and
   reading of the height of the flame on a scale graduated in mm,
   characterized in that a series of digital images of the flame is taken and stored using a digital camera or an equivalent of such a camera, at intervals that are sufficiently close to enable, by analyzing these digital images, the detection of a sudden change in the shape of the flame, and measuring the height of the flame at the moment of the sudden change in its shape, said height being considered as the smoke point of the hydrocarbon under test.

2. The method as claimed in claim 1, characterized in that the digital camera comprises a photodetecting charge-coupled device (CCD).

3. The method as claimed in claim 1, characterized in that the image-taking intervals are between 0.1 and 2.0 seconds.

4. The method as claimed in claim 1, characterized in that the detection of the sudden change in the shape of the flame is achieved by measuring the sudden change in the speed of reduction of the Feret diameter of the image of the flame.

5. The method as claimed in claim 4, characterized in that, to detect the sudden change in the speed of reduction of the Feret diameter, this Feret diameter is measured at an angle $\alpha$ less than 45°.

6. The method as claimed in claim 4, characterized in that the height of the flame is equal to the Feret diameter for $\alpha=0°$ of the image of the flame.

7. The method as claimed in claim 6, characterized in that the digital image corresponding to the sudden change in the speed of reduction of the Feret diameter is subjected to a thresholding operation using a determined threshold with the help of one or more standard fuel mixtures (toluene/2,2,4-trimethylpentane) with known smoke point (ASTM D 1322).

8. The method as claimed in claim 1, characterized in that the charge-coupled device (CCD) digital camera covers wavelengths ranging from the ultraviolet to the infrared.

9. The method as claimed in claim 1, characterized in that an anti-infrared filter is placed between the flame and the CCD digital camera.

10. The method as claimed in claim 1, characterized in that the digital camera with CCD stores digital images with at least 512 gray levels.

11. The method as claimed in claim 1, characterized in that a CCD digital camera with zoom is used and that this camera is placed at a distance of approximately 1 m to 1.5 m from the lamp.

12. The method as claimed in claim 11, characterized in that the zoom is set so that the stored digital image contains the image of all the graduated scale of the device for determining the smoke point.

13. The method as claimed in claim 1, characterized in that the number of digital images of each series is at least equal to 10.

14. The method as claimed in claim 1, characterized in that the digital image-taking operations and the analysis and processing of these images are automated using a dedicated software package.

15. A device for determining the smoke point of a hydrocarbon fuel, comprising:
   an apparatus for determining the smoke point conforming to the specifications of the ASTM D 1322 standard,
   a digital camera, and
   a computer system linked to said camera and designed and programmed to enable digital images taken by the digital camera to be stored, analyzed and processed.

16. The device as claimed in claim 15, further comprising an anti-infrared filter placed between the apparatus for determining the smoke point and the digital camera.

17. The device as claimed in claim 15, characterized in that the digital camera covers wavelengths ranging from the ultraviolet to the infrared.

18. The device as claimed in claim 15, characterized in that the digital camera stores digital images with at least 512 gray levels.

19. The device as claimed in claim 15, characterized in that the digital camera comprises a zoom and is placed at a distance of approximately 1 m to 1.5 m from the lamp of the apparatus for determining the smoke point.

20. The device as claimed in claim 19, characterized in that the zoom is set so that the stored digital image contains the image of all the graduated scale of the apparatus for determining the smoke point.

21. The method as claimed in claim 1, characterized in that the image-taking intervals are between 0.5 and 1.0 second.

22. The method as claimed in claim 1, characterized in that the digital camera with CCD stores digital images with at least 32 768 gray levels.

23. The device as claimed in claim 15, characterized in that the digital camera stores digital images with at least 32 768 gray levels.

* * * * *